United States Patent [19]

Coleman et al.

[11] Patent Number: 5,065,768
[45] Date of Patent: Nov. 19, 1991

[54] SELF-SEALING FLUID CONDUIT AND COLLECTION DEVICE

[75] Inventors: Charles M. Coleman, Pittsburgh; William G. Kendrick, Sr., Doylestown, both of Pa.

[73] Assignee: Safe-Tec Clinical Products, Inc., Ivyland, Pa.

[21] Appl. No.: 243,982

[22] Filed: Sep. 13, 1988

[51] Int. Cl.⁵ .............................................. A61B 5/00
[52] U.S. Cl. ................................. 128/760; 73/864.02
[58] Field of Search ............... 128/760, 763, 765, 766, 128/770; 73/864.02, 864.03; 604/15, 21, 51, 52, 126, 134–136, 187, 90, 218, 226; 279/41 R

[56] References Cited

U.S. PATENT DOCUMENTS

| 3,238,941 | 3/1966 | Klein et al. | 604/218 |
| 3,480,014 | 11/1969 | Callahan | 604/51 |
| 3,741,732 | 6/1973 | Stanfield | 73/425 |
| 3,750,667 | 8/1973 | Pshenichug et al. | 604/117 |
| 3,783,696 | 1/1974 | Coleman | 73/425 |
| 3,864,979 | 2/1975 | Ayres | 73/864.02 |
| 3,891,392 | 6/1975 | Betts et al. | 73/864.02 |
| 3,952,599 | 4/1976 | Ayers | 73/425 |
| 3,960,139 | 6/1976 | Bailey | 128/2 |
| 3,995,496 | 12/1976 | Bickford | 73/864.03 |
| 4,027,660 | 6/1977 | Wardlaw et al. | 73/425 |
| 4,082,085 | 4/1978 | Wardlaw et al. | 73/425 |
| 4,122,947 | 10/1978 | Falla | 128/760 |
| 4,133,304 | 1/1979 | Bailey | 128/2 |
| 4,137,755 | 2/1979 | Wardlaw et al. | 73/61.1 |
| 4,159,896 | 7/1979 | Levine et al. | 23/230 |
| 4,190,328 | 2/1980 | Levine et al. | 350/320 |
| 4,267,729 | 5/1981 | Eddleman et al. | 73/864.02 |
| 4,657,454 | 4/1987 | Migita et al. | 279/41 R |
| 4,781,683 | 11/1988 | Wozniak et al. | 604/110 |

FOREIGN PATENT DOCUMENTS

| 0067726 | 12/1982 | European Pat. Off. | 128/760 |
| 0166574 | 1/1986 | European Pat. Off. | |
| 0176080 | 4/1986 | European Pat. Off. | |
| 2176711 | 1/1987 | United Kingdom. | |

OTHER PUBLICATIONS

"Quantitative Buffy Coat Analysis, A New Laboratory Tool Functioning as a Screening Complete Blood Cell Count", by Wardlaw and Levine, 1983.
Chemical Abstract 105: 80370h, Feb. 1986.
Chemical Abstract 105: 99323d, Feb. 1986.
Chemical Abstract 105: 135280y, Oct. 1984.
Chemical Abstract 105: 6575v, Jul. 1986.
Article "Simikagel SP-520 High Absorptivity Polymer", Nov. 1984.
Brochure "Aridall 1080 Superabsorbent Polymer", Mar. 1987.
Fisher Scientific Catalog 1986, pp. 407, 409.
Lancer Laboratory Supplies Catalog, 1981, by Sherwood Medical.

Primary Examiner—Max Hindenburg
Attorney, Agent, or Firm—Buchanan Ingersoll

[57] ABSTRACT

A self-sealing fluid collection tube is provided with an elongated bore and a fluid entry end. A plug of superabsorbent material is provided within the tube opposite the fluid entry end. This plug is preferably vented and is adapted to seal the tube by expanding when contacted by a fluid, such as blood. After the fluid has been collected, the tube is placed in a pipetter-dispenser in which a plunger, which is inserted into the tube, moves through a calibrated distance thereby advancing the plug into the tube and expelling a selected volume of fluid from the tube. Alternatively, the fluid may be transferred into another receptacle by piercing the sealed plug to form a new vent channel to permit drainage of the collected fluid into a receptacle.

27 Claims, 1 Drawing Sheet

5,065,768

SELF-SEALING FLUID CONDUIT AND COLLECTION DEVICE

BACKGROUND OF THE INVENTION

1. Field of the Invention

The present invention relates to a method and apparatus for the handling and control of fluids in conduits, particularly small bore tubes, with new and novel plugs adapted to seal on contact with the fluid. More specifically, the present invention relates to the collection of aqueous fluids, such as blood, in small bore tubes. Additionally, the present invention relates to a conduit which will automatically seal itself after collection of the fluid, to a dispenser-pipetter which cooperates with the plug to dispense precise micro-volumes of a fluid from the collection tube, and to a small bore collection tube fitted with a venting puncture cap that permits transfer drainage of the contents of the collected specimen into a receptacle.

2. Description of the Prior Art

It is well known in the art to collect and centrifuge fluids, such as blood, in small bore or capillary tubes in order to determine the fraction of the cellular constituents relative to the total volume of blood. This is known as the packed cell volume or the hematocrit. In the Approved Standard of the National Committee For Clinical Laboratory Standards (NCCLS) known as the "Microhematocrit Method", capillary blood collection tubes are sealed immediately after collection of the blood. Generally, the tubes are sealed by pressing the thin capillary tube into a layer of clay-like sealing compound provided in small trays, five to seven millimeters in depth. Subsequently, the tubes are centrifuged and the ratio of the height of the red blood cells to the total height of the blood column, which includes all the cells (red and white) plus the light phase, also called the serum or plasma, is determined. This ratio, expressed as a percentage, is called the hematocrit value, and decimally, as the packed cell volume.

This procedure to obtain the hematocrit value by the widely used Approved Standard Microhematocrit Method provides a significant health risk to the laboratory worker or other medical personnel conducting the test. The capillary collection tubes are specified by the NCCLS to be within certain tolerances. Current specifications require a tube seventy-five millimeters in length, 1.155 millimeters in internal diameter, and the wall 0.2 millimeters thick. Present tubes are made of glass and are readily breakable. Glass tubes have broken when a technician presses the tube into a sealing compound. If a tube breaks, broken glass may penetrate the finger of the laboratory worker, thereby inoculating the blood within the tube into the worker. If this happens, the worker is at high risk of infection with viruses or whatever infectious units are present in the collected blood. Thus, there is a need for an integrated capillary collection tube that eliminates the hazardous step of pressing the device into a sealant after the blood is collected.

We have found that it is possible to collect skin puncture blood specimens directly into narrow bore (0.5-0.6 mm) capillary tubes, such as Becton, Dickinson's Pre-Cal Micro-Hematocrit Tubes providing that they are plugged with the conventional clay-like sealing compound recommended by the NCCLS, if a vent channel of about 0.2 mm diameter is present, and if extraordinary precautions are made to maintain the collection tube horizontal from the initial collection stage, through the placement of the tube within a Microhematocrit Centrifuge that has been specially fitted with a soft rubber padding band directly inside the standard base band for the capillary tubes. It is noted that this extraordinary procedure requires special care and meticulous handling, and that there is no margin for error. The consequences of failure are loss of blood from the inside of the tube, with contamination of the environment. It is a very hazardous procedure, with nothing to recommend it as it stands.

It has also been the practice in the past that, when processing small volumes of centrifuged blood for chemical or serological testing, technicians have removed serum or plasma from the collection vessel and manually measured the amount desired using a pipet or a pipetter-dispenser. This requires the use of two vessels: the collection vessel and the dispensing vessel. An integration of these vessels would result in economy of operator time and materials. By reducing exposure to the blood, such a device would reduce the risk of blood-borne infections. Therefore, there is a need for a single vessel which combines the operations of collection, separation, and micro-volumetric dispensation of blood.

It is further known that certain water absorbing polymers that are covalently cross-linked or possess ionic interaction between polymer chains, designated "super-absorbents", have high water absorbancy characteristics which cause them to expand greatly, forming gel particles in the presence of water. These are designated by some as hydro-gel. These products are used widely to absorb water from body fluids and have been incorporated in personal hygiene products such as infant's diapers and women's sanitary products. They are also used as water-retaining materials for agricultural mulches. In a finely divided form and combined with rubber or elastomers, these super-absorbents have been used in well-drilling operations to stop leaks in pipes, and with rubber, elastomers and/or other organic resins to make water swelling paints, pastes, gaskets, coatings of electrical wires, and other products having unique water-swelling and water-retaining properties. Super-absorbent composite materials have been developed which can expand by water imbibition more than 25 times their original volume, depending on conditions. Composites of super-absorbent polymers with resins and elastomers are formulated to provide greatly enhanced strength and other physical properties which the super-absorbent's weak hydrated gel structure does not possess when used alone.

SUMMARY OF THE INVENTION

The present invention comprises an apparatus and method for the collection of fluid with the option of separation and/or dispensation. The apparatus includes a collection tube and, optionally, a pipetter-dispenser, or a specimen transfer tube, consisting of a collection tube fitted with a vent channel puncture means to permit air reentry into the tube and subsequent fluid drainage of the collection tube. The collection tube includes a self-sealing fluid collection tube having a unitary tubular body, which preferably is either a glass or organic polymer. The tubular body is provided with an elongated bore and a fluid entry end. A super-absorbent plug composed of a of water-swellable material is provided within the tube opposite the fluid entry end. This plug is adapted to imbibe water and swell (expand) when contacted by an aqueous fluid and seal the tube. A vent channel is provided within the plug to allow air within the tube to escape when fluid enters. Expansion of the plug causes the vent channel to constrict, thereby blocking any further venting and stopping flow of fluid into the tube.

The present invention is ideally suited for the microcollection of body fluids, especially blood, in capillary and other small bore tubes. It is particularly useful for blood obtained by means of a skin puncture. If the collection tube is intended to have its contents separated by centrifugation, the plug, which is generally formed from a composite, should have a specific gravity greater than that of the blood cells. If the plug is comprised of a material which bonds or strongly adheres to the tube wall, the specific gravity of the plug may not be important. Upon centrifugation, the plug is deformed under compression, thereby improving the seal resulting from the swelling of the plug caused by the contact with the blood.

We have found that various organic polymers and materials, such as beeswax, organic oils such as silicones, hydrocarbons, esters, and the like, rendered thixotropic by addition of finely dispersed agents, such as amorphous silica gel and solid fats, can serve as organic matrices for the super-absorbent polymers. For blood collection tubes, the specific gravity of these materials should be generally greater than about 1.09 (the density of the blood cells, the heaviest component of the blood) and the material should have sufficient compliance to compress and form a seal at a level of centrifugal force generally adequate to determine the packed cell volume. We have found that the best results are obtained using a mixture of a finely divided cross-linked acrylic acid polymer within a support polymer matrix. In a preferred embodiment, a co-polymer of acrylic acid and vinyl alcohol is mixed into a rubber matrix. The polymer preferably is about 60 microns or less in diameter and cross-linked. Other super-absorbent materials composed of acrylic acid such as the homopolymers of acrylic acid are also effective when reduced to about 20 to 40 microns mean diameter. Moreover, super absorbents, such as starch-acrylic acid graft polymers and acrylic acid block co-polymers also may be used when dispensed within a support matrix.

A gel separator element, such as that used in a vacuum blood collection tube for the collection and separation of venous blood, may be placed within our capillary tube having a self-sealing plug at one end. The gel is preferably in the form of a short rod segment and is provided along one side of the tube wall. Alternatively, a ring of gel may be provided near or in contact with the self sealing plug. The separator gel has a specific gravity intermediate the light phase and heavy phase of the blood. Upon centrifugation, the gel proceeds to the interface of the light and the heavy phases of the blood to form a seal therebetween. This embodiment is used when it is desired to maintain the light and heavy phases of the blood isolated from each other for an extended period of time.

If one desires to use our tube for storing blood, he may want to reduce the imbibition of water into the plug from the blood after centrifugation. This can be done by adding to the tube a grease or other material having a specific gravity between the specific gravities of the plug and the blood. When blood enters the tube it will contact the plug to make it swell and seal. After centrifugation the added material will form a barrier between the blood and the plug thereby blocking water flow from the blood into the plug.

The collection tube may be used in a specimen transfer mode without centrifugal separation if a vent channel puncture means is incorporated into the collection device. A simple integrated device would add a cap at the end of the tube and closely adjacent to the sealed self-sealing plug. The tube will hold the aqueous specimen in the tube by air pressure when the specimen is collected, the fluid contacts the vent channel, and the plug thereupon sealed. When it is desired to transfer an unseparated specimen, such as is the case with microspecimens for blood gas analysis, a hypodermic needle, or a small bore molded cannula with sharper point is pressed through the plug to permit air flow to proceed through the sealed plug, and allow transfer of the collected fluid out of the collection tube, and into the receptacle. Preferably, this needle is incorporated into a cap which fits over the plugged end of the tube. This is the simplest way to dispense collected specimens, but not the most precise.

Preferably, a pipetter-dispenser is used to dispense a measured quantity of collected fluid. The pipetter-dispenser has a housing having a thin rod member extending axially therethrough. The rod member is adapted to fit within a collection tube. One end of the rod member is attached to a plunger which extends out of one end of the housing. Stop means are provided on the plunger to permit the plunger to travel through a calibrated distance. The opposite end of the housing is provided with a collet which locks the capillary tube in place within the elongated body.

We have found that it is preferable, but not essential, for the collection-separation-dispensation mode tube to have a slight flare at the end nearer the plug. In use, the flared end of a precision bore capillary tube is inserted into the pipetter-dispenser in such a way that the rod member extends into the tube and abuts the plug. The rod member should push against the super-absorbent plug until the fluid is at the end of the tube or at another selected position within the tube. At this point, the tube is locked in place by means of the collet. As the plunger is depressed, the rod member extends further into the capillary tube and pushes against the plug located at the end of the capillary tube. Because the distance the plunger travels has been calibrated, a known and precise amount of fluid is expelled. If the plug is intended to be moved by a dispenser, the plug should not bond to the tube wall. Bonding can be prevented by appropriate selection of materials for the plug, or use of a release agent on the inner wall of the tube.

The capillary tubes used with the pipetter-dispenser can be formed from molded or extruded synthetic resins or elastomers. Alternatively, the tubes can be opaque tubes formed from metal or ceramic materials. Moreover, the tubes can be formed from the glass which is specified by the American Society for Testing Materials (ASTM) as the standard for capillary tubes used in the NCCLS Microhematocrit Method. Finally, a glass capillary tube that is covered by a polymer protective film or tubular sheath can be used. Such film or tubular sheath, if clear, would enable the contents of the tube to be visually or photo-optically examined, while protecting the user from injury that might occur upon handling and centrifugation of the tube. Such a sheath can be used to provide even further protection for the user from accidental injury from glass particles that might be released upon centrifugation.

With the use of the new and novel self-sealing plug in collection tubes intended to handle biological specimens there are several options of usage combinations. First, the plug can be used to form a self-sealing micro-hematocrit tube for the collection and centrifugal separation of blood. This provides an apparatus for a simplified and safe determination of the packed cell volume. Second, the plug can be used to form a tube which provides for the integration of the collection, separation, and micro-volumetric dispensation of either blood plasma or blood serum. Third, the self-sealing plug may be used in a tube simply to collect and hold blood. A disposable Wintrobe Tube of this sort can be used to determine the Erythrocyte Sedimentation Rate, wherein the self-sealing plug is substituted for the usual cotton plug. Fourth, the self-sealing plug used in the collection tube may be revented. In this mode, the tube may be used as a transfer device i.e., both for the collection of the specimen, and the subsequent drainage of the tube contents into a desired receptacle. Such a situation occurs when micro quantities of blood are collected for blood gas analysis. The collection tube may be fitted with a cap holding a narrow gauge cannula, such as a 27 gauge hypodermic needle, poised above and pointed toward the self-sealed plug. When it is desired to release the contents of the tube (which may be held "upside down" within the tube by air pressure in conjunction with surface tension), into the desired receptacle, the cap is pressed, the hollow needle penetrates the plug, the air pressure supporting the fluid is nullified by air entering at the opposite end and the specimen drains from the collection tube into the receptacle as a consequence of the gravitational force causing outward flow. Several blood gas analysis apparatus instruments can use this type of tube. Finally, the self-sealing plug may be used in a capillary tube for the collection of aqueous fluids followed by direct dispensation of the unseparated fluid. Such may be desired for micro-volumetric dispensation of capillary collected blood into hematological counters, or onto dry strips that use whole blood. Urine may also be handled in this manner, wherein it is collected and then dispensed, without separation by use of a pipetter-dispenser or vent tube penetration of the sealed plug.

A BRIEF DESCRIPTION OF THE DRAWINGS

DESCRIPTION OF THE PREFERRED EMBODIMENTS

Figure 1:
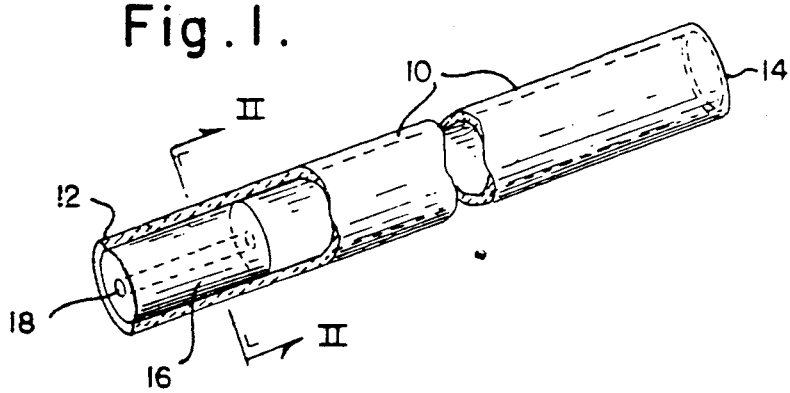
FIG. 1 is an fragmentary isometric view of a first present preferred embodiment of the fluid collection tube of the present invention.
Figure 2:
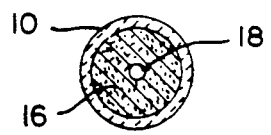
FIG. 2 is a cross-sectional view of the fluid collection tube of FIG. 1 taken along the line II—II.

A system for the collection, separation and dispensation of a fluid is provided which includes fluid collection tube 10 and pipetter-dispenser 50. As shown in FIGS. 1 and 2, fluid collection tube 10 is preferably provided with plug-end 12 and opposite end 14. The fluid to be collected enters tube 10 through opposite end 14. Preferably, tube 10 is in the form of a capillary tube. However, tubes 10 of various sizes and shapes can be used.

Figure 3:
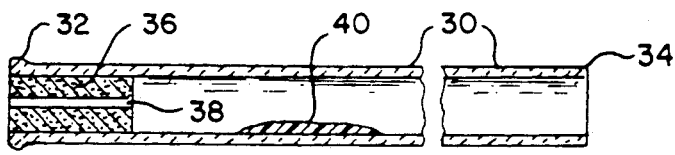
FIG. 3 is a sectional view of a third present preferred embodiment of the fluid collection, separation, and dispensation tube of the present invention.
Figure 4:
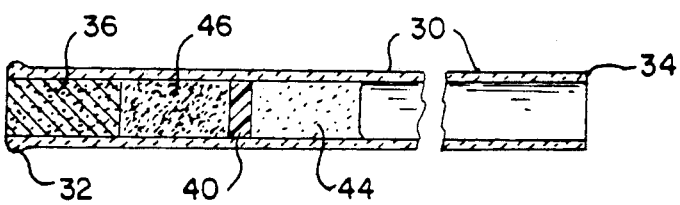
FIG. 4 is a sectional view of the fluid collection tube of FIG. 3 after collection and centrifugation of a non-homogeneous fluid.

A plug 16 of super-absorbent material is provided at the end 12 of the fluid collection tube 10. A vent channel 18 is provided axially within plug 16 to provide an outlet for the gas displaced during fluid collection. Alternatively, plug 16 may be formed so that a vent channel is formed by a gap between plug 16 and the inner wall of tube 10. This vent channel permits air displacement when the tube fills with a liquid. When used in a capillary tube, vent hole 18 is necessary to permit air displacement so that fluid may flow into tube 10. Alternatively, and preferably when dispensation is intended, a slightly flared end 32 is provided, as shown in FIGS. 3 and 4.

As the fluid enters tube 10 and reaches the end 12 of tube 10, it causes the vent channel 18 provided in plug 16 of super-absorbent composite material to imbibe, swell, and constrict. As the plug 16 swells, it constricts and closes vent channel 18 and seals end 12. In this manner, fluid collection tube 10 provides an efficient means to collect a fluid.

Figure 5:
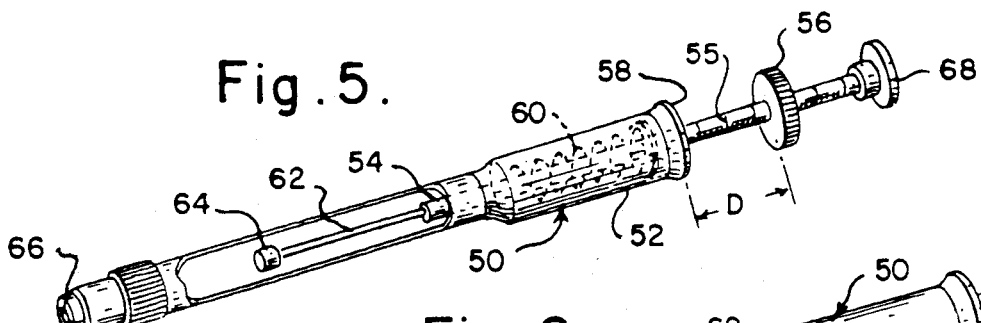
FIG. 5 is an perspective view partly in section of the pipetter-dispenser of a preferred embodiment of the present invention.

Fluid collection tube 10 is formed by inserting the plug 16 of super-absorbent composite material into the end 12 of a standard capillary tube 10. Alternatively, if hand micro-volumetric dispensation of fluid is desired, a tube 30, as shown in FIGS. 4 and 5 having a length of 75 mm and an inner diameter of 1.25 mm or greater is preferred so that a greater volume of fluid could be used. We have found that the thickness of the tube wall of a glass tube should be about 0.3 mm to accommodate the pressure exerted against plug 36. Preferably, plugs 16 and 36 are approximately 3.2 mm to 6.4 mm in length and substantially fill the inner diameter of tubes 10 and 30. Vent channel 18 is provided through the plug 16 by inserting a thin wire therethrough. Preferably, vent channel 18 is approximately 0.1 to 0.2 mm in diameter. Such a vent channel 18 would provide a sufficient cross-sectional area for the displaced air to exit the capillary tube 10. The vent channel 18 may be of any cross-sectional shape although we prefer to use round and oval shapes.

Fluid collection tube 10 is ideally suited for the micro-collection of blood in a capillary tube. Preferably, the super-absorbent composite material in collection tube 10 has a specific gravity greater than that of the heaviest component of the blood.

Alternatively a disposable capillary collection tube which is generally recommended for the Microhematocrit Method by the NCCLS can be used as tube 10. Such a tube, which should meet ASTM specifications is preferably 75 mm±0.5 mm in length, has an internal diameter of 1.155±0.085 mm and has a wall thickness of 0.2 mm. This tube is composed of borosilicate glass, type I, class B, or soda lime glass, type II, with specifications on taper. However, tubes of various lengths, inside diameters, and markings can be used.

Becton, Dickinson and Company markets a capillary tube for use in the hematocrit determination that is provided with an inside diameter of smaller diameter than the ASTM standard capillary tube. This tube has a thicker wall and is marked to fill a blood column 60 mm in length. These tubes may be fitted with the self-sealing plugs of this invention. The plugs of this invention can also be used with tubes that handle other aqueous fluids. Such tubes are extruded or molded from organic polymers and are preferably provided with a hydrophilic surface. In addition, the plugs of this invention may be used with tubes that are coated with a polymer film jacket or which have a shrinkable tubing placed over the glass capillary tube.

The Disposable capillary tube operates in a similar manner to fluid collection tube 10. A plug of super-absorbent material is provided at one end of the tube. The fluid to be collected enters the tube through the opposite end. A vent channel is provided within the tube to provide an outlet for the gas displaced by the collected fluid.

A variety of compounds can be used as the super-absorbent. A super-absorbent polymer mixed with an organic carrier material or matrix provides the appropriate swelling characteristics and strength required for the plug. A mixture of rubber and acrylic acid, such as a cross-linked acrylic acid or an acrylic acid grafted onto starch or copolymers of acrylic acid/vinyl alcohol cross-linked, or acrylic acid containing block co-polymers perform well in sealing the collection tubes under most circumstances. In the preferred embodiment next described, such a composition is capable of swelling 25 or more times its original size in distilled water and 8 or more times in blood.

Present preferred embodiments of our composite containing a super-absorbent polymer are set forth in the following examples.

EXAMPLE I

Five grams of Dow-Corning "100% Silicone Rubber General Purpose Sealant, Clear", obtainable from hardware stores, was mixed with five grams of Sumikagel SP520 supplied by the Sumitomo Chemical Company of Tokyo, Japan, and the two ingredients were thoroughly blended to yield a soft, putty-like composite material in which the Sumikagel SP520, an acrylic/vinyl co-polymer, sodium salt, about 20 to 30 microns in size, was dispersed throughout the room temperature vulcanizing silicone rubber matrix. Capillary tubes, both of the type used for the Microhematocrit Method, and precision bore tubes for use in collection, centrifugal separation, and microvolumetric dispensation were found to be easily plugged by the same simple method as used in sealing the tubes with the clay-like sealant recommended in the NCCLS Microhematocrit Method. Soon after a plug of 3.2 to 4.8 mm. in length was pressed into the tube, a wire of 0.2 mm diameter was forced through the axial part of the plug, and withdrawn. The tubes were then set aside to cure over a period of three days at 20° to 23° C. When the self-sealing plug is made for use with tubes intended for dispensation of centrifugally separated plasma or unseparated biological fluids (as whole blood), a mold release agent is desirable. General Electric Silicone II Sealants were found to be equally effective when purchased from retail hardware stores and properly blended with acrylate super-absorbent polymers. Finely divided Aridall 1125, sold by the Chemdal Corporation of Arlington Heights, Ill., has also been found to be satisfactory when reduced in size to particles of 40 microns, or less, and then blended with raw rubber stock and plasticizers. The Aridall 1125 is a cross-linked homopolymer of acrylic acid, potassium salt, and is preferably blended to give a final concentration of about 50% by weight in the ensuing elastomer composite. The specific gravity of the self-sealing plug is preferably greater than the heaviest component (in blood, the red blood cells) unless the rubber adheres tenaciously to the inner wall of the tube. The material must be firm enough to maintain a vent channel. The material must also be compounded so that a smooth plug is formed that is in full contact with the wall of the tube. The procedures to be used in mixing and blending the rubber or rubber-like material and the finely divided super-absorbent materials, with additional processing aids and compounding ingredients, such as plasticizers and pigments are well known and commonly used by those skilled in the art of rubber compounding.

EXAMPLE II

A black composite is suitable for use in tubes 10 and 30. However when the tube is used for blood collection there is less contrast between the plug and the blood. The Oyo Corporation of Japan sells an aggregate mixture called "Nistop", which is expressly intended to retain ground water from entering bore holes drilled for oil and gas exploration. The aggregate consists of black lumps and pieces, generally 3 mm and larger, dispersed within granules of a super-absorbent polymer. The black lumps are a composite comprised essentially of a finely divided acrylic acid polymer dispersed within an elastomeric material and carbon black. The acrylic acid polymer is Sumikagel SP520.

The black viscoelastic super-absorbent composite in the Nistop aggregate is satisfactory for the fabrication of self-sealing plugs for the collection, separation, and dispensation of microvolumes of the plasma phase of collected blood. The black Nistop material can be used for the determination of the packed cell volume, excepting that its dense blackness makes poor contrast against the border of the dark red packed blood cells. This make it difficult to distinguish the baseline (zero value).

Other water-swellable rubbers, both vulcanized, and unvulcanized may be used. We have found some compositions manufactured by Seitetsu Kagaku to be acceptable. These were water-swellable rubber compounded with styrene-butadiene rubber, and nitrile-butadiene rubber, unvulcanized, containing Sumikagel SP520, and carbon black. Both were found to make self-sealing plugs which were jet black, and to have self-sealing functions.

Our self-sealing plugs may be formed in situ, as have the ones generally described above in these specifications. They also may be made by extrusion, and co-extrusion processes, and injection and other molding procedures. The extruded tubing, with a vent channel must have sufficient strength to hold its shape during the manufacturing, and intended functions. Co-extruded tubing can be utilized for making plugs with the proper strength, lubricity, and other properties needed for contact with the tubular surfaces inside which the self-sealing plug is positioned. This is especially true if the self-sealing plug is operating as a piston is moved by a push rod. Those skilled in the art will recognize that there are a multitude of ways in which the self-sealing plug may be manufactured. The particular method selected will likely depend upon equipment availability and other process factors.

Tubes may be used for collection and dispensation of fluid without the intermediary operation of separation. After blood fills to the self-sealing plug 16, it may be measured out micro-volumetrically with a pipetter-dispenser into any diagnostic field such as a dry chemistry strip, or into a measured volume of diluent for hematological testing.

A further embodiment of our collection tube can be seen in FIG. 3. In this embodiment, fluid collection tube 30 has a fluid entry end located at opposite end 34. Plug 36 of a super-absorbent containing composite material is provided in the slightly flared end 32 of blood collection tube 30. Vent channel 38 is provided through plug 36 to vent tube 30 to permit capillary action. This vent channel will close when blood or another fluid comes in contact with it. The super-absorbent composite material used in plug 36 is selected so that the specific gravity of plug 36 is heavier than that of the heavy phase of blood. Interphase gel sealant material 40 is provided alongside the inner wall of tube 30. Gel sealant material 40 is chosen such that its specific gravity is intermediate that of the light and heavy phase of the blood.

After blood has been introduced into fluid collection tube 30, tube 30 can be centrifuged to separate the blood into its light and heavy phase components. Centrifugation will cause interphase gel to move from the sidewall to the position shown in FIG. 5. FIG. 4 shows tube 30 after it has been centrifuged. After centrifugation, sealant 40 is located intermediate the light phase 44 and heavy phase 46 of the blood. Plug 36 remains at slightly flared end 32 of tube 30, sealed, compacted, and adjacent the heavy cellular phase 46 of blood. In this manner, tube 30 can be used in the collection and sealed separation of the blood.

Figure 6:
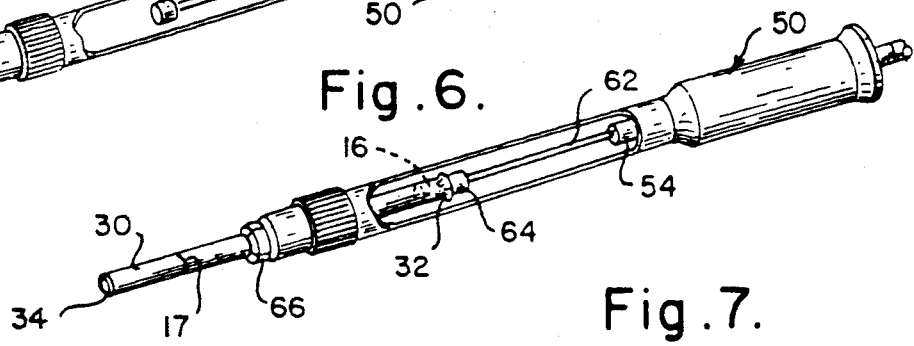
FIG. 6 is a partial perspective view partly in section showing the capillary tube of FIG. 4, after it has undergone centrifugation, inserted into the pipetter-dispenser of FIG. 5 for operation.

In order to dispense a measured volume of fluid from collection tube 10 or 30, we provide a dispenser 50 as shown in FIGS. 5 and 6. Pipetter-dispenser 50 includes elongated body 52 through which thin rod member 62 axially extends. Preferably plug 64 is provided at one end of rod member 62. Alternatively, rod member 62 could be made large enough in diameter so that plug 64 is not needed. The opposite end of rod member 62 is attached to plunger 54 which extends out of one end 58 of housing 52. Stop means 56 is provided on plunger 54 and permits plunger 54 to travel through a calibrated distance. Stop means 56 can be permanently attached to plunger 54 or it can be in the form of a set screw which can be positioned along plunger 54 and calibrated according to scale 55. A locking collet 66 is provided on the end of housing 52 opposite end 58 and is adapted to lock capillary tube 10 within pipetter-dispenser 50.

When knob 68 is depressed, plunger 54 is forced into housing 52. The abutment of stop means 56 against end 58 of housing 52 causes plunger 54 to stop its descent. Because the distance "D" between extended stop means 56 and end 58 has been calibrated, plunger 54 moves a known distance when fully depressed. Spring 60 acts on plunger 54 to force plunger 54 back out of housing 52.

In use slightly flared end 32 of capillary tube 30 is inserted into pipetter-dispenser 50 such that rod member 62 can extend into the tube 30. Tube 30 is then pushed into pipetter-dispenser 50 until the serum or plasma component of the blood is at the end 34 of the tube or at calibration line 17. Thereupon, tube 30 is locked in place by turning collet 66. As plunger 54 is depressed, rod member 62 extends further into capillary tube 30 and plug 64 pushes against plug 16 located within the capillary tube, thereby expelling blood serum or plasma. Because the distance which plunger 54 travels has been calibrated, a known and precise amount of fluid is expelled.

An added advantage of our invention is that identical multiple samples of blood plasma or serum can be obtained when the tube 30 has a constant inner diameter. After each depression of plunger 54, tube 30 is positioned within housing 52 in accordance with the procedure set forth above. Limited only by the amount of serum or plasma remaining in tube 30, plunger 54 can be depressed a number of times to produce a number of samples having identical quantities of blood or serum therein. Consequently, a number of different tests can be performed on the blood collected in a single capillary tube.

Although our invention has been described in relation to its use for precise measurement, our pipetter-dispenser 50 can be used as an ordinary fluid dispenser. Even if a tube 30 having an irregular inner diameter is used to collect the fluid, the dispenser 50 will nevertheless expel a volume of fluid. Such a use of our invention is appropriate where exact volumes of fluid to be tested are not required.

It should be obvious that this invention may also be used for the two steps of collection and dispensation of micro-volumes of unseparated fluid, such as whole blood in those circumstances where minimal contact of the blood is required, yet an accurate dispensation of whole blood is needed. This requirement prevails in hematological studies where electrochemical counting of diluted whole blood, and other studies are made. The self-sealing plug permits collection in a self-sealing tube, with the rod propulsion of the plug. Some analytical systems, especially with the use of dry chemistry testing strips, utilize whole blood, yet need a moderately precise micro-volume of blood dispensed onto the strip.

In those cases where it is desired to collect and transfer whole blood for certain uses, such as blood gas determinations and where it is not desired to either separate the blood, or unnecessary to pipet exact volumes of blood, the addition of a reventing cap to a collection tube with self-sealing plug permits the collection and transfer of the collected specimen by drainage of the collected column of fluid by gravity. The penetration and reventing of the sealed plug counterbalances the air pressure, i.e, the vacuum hold on the fluid column is broken and the specimen flows into a receptacle. In the case of a micro blood gas specimen, the capillary tube filled with blood for a blood gas determination is connected with a reception tube input of a micro blood gas analysis machine.

Figure 7:
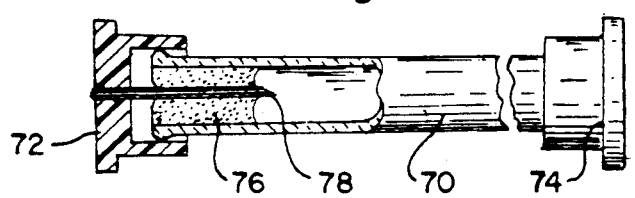
FIG. 7 is an elevational view of our collection tube fitted with a reventing cap to form a transfer tube.

FIG. 7 shows micro blood gas tube (transfer tube) 70 sealed and filled with heparinized blood. A reventing cap 72 is slidingly provided adjacent the sealed self-sealing plug 76. Closure cap 74 is fitted at the blood entry end. The tube is revented by sliding reventing cap 72 inward along tube 70 thereby piercing the self-sealing plug 76 with 27 gauge hypodermic needle 78 attached to reventing cap 72. Needle 72 is preferably 13 mm in length.

Identification means can be added to the capillary tube 10 of this invention to provide safeguards against misdiagnosis of a patient's condition. The identification means can consist of a label provided directly on tube 10 or on a cover cap which is adapted to fit over end 14 of the tube 10. Further protection is obtained by using both of these identification means. Proper use of the identification means prevents a sample from one patient being confused with that of another, thereby preventing a misdiagnosis from occurring by testing of his labeled sample.

In this specification, we have used blood as an example of the type of a fluid to be tested which can be collected within small bore tubes. However, it is to be understood that the present invention relates to any aqueous fluid which can be collected and tested. Also, in this specification we have used a capillary collection tube as an example of a vessel which can collect fluid. It is to be understood that the present invention relates to and can be adapted for use with any vented tubular device or a device having a tubular portion which can collect, separate, dispense or transmit fluids. Such containers include capillary blood collection tubes, microhematocrit capillary tubes, Caraway capillary tubes, urine sediment tubes, small bore tubes, blood gas determination tubes, capillary tubes, capillary tubes for blood collection, blood chemistry determination tubes, Wintrobe sedimentation pipets and Natelson capillary tubes, and preloaded Quantitative Buffy Coat determination tubes of Wardlaw, Levine and Massey, with interphase floats and fluorescent dyes of the type sold by Becton, Dickinson and Company.

In addition, aqueous fluid that may be utilized in fluid transmission tubes, which require certain safety check valves, can utilize the self-sealing plug element of this invention where single use check valves are required.

The collection tubes described above may also be used with anti-coagulants, such as heparin (and its various cation salt derivatives), or with clotting accelerators such as prothrombin. When plasma is dispensed, specific agglutinating substances, such as antibodies or phytoagglutinins, added by coating of the tube walls, to aid in holding the cells together during dispensation, may be included in the device of this invention.

While we have described certain presently preferred embodiments of our invention, it is to be distinctly understood that the invention is not limited thereto and may be otherwise variously practiced within the scope of the following claims.

We claim:

1. A self-sealing tube comprising a tubular body having an elongated bore and a fluid entry end, and a movable plug of super-absorbent containing composite material provided within said tube, said super-absorbent material adapted to expand when contacted by an aqueous fluid and seal said tube to prevent passage of air and liquids through the plug during centrifugation and expulsion.

2. The tube of claim 1 wherein said plug has an opening provided therein, said opening sized to vent said tube when fluid enters said tube, said opening being closed by the expansion of said plug of super-absorbent material when contacted by said aqueous fluid.

3. The tube of claim 2 wherein said super-absorbent material comprises a super-absorbent polymer and an organic support matrix.

4. The tube of claim 3 wherein said super-absorbent polymer is an acrylic acid containing polymer.

5. The tube of claim 4 wherein said organic support matrix is a member of a class consisting of organic polymers, fats, waxes and thixotropic oils blended into a composite material.

6. The tube of claim 1 wherein said plug of super-absorbent material has a specific gravity greater than the heaviest component of the fluid.

7. The tube of claim 6 wherein said super-absorbent material comprises a super-absorbent polymer and an organic support matrix.

8. A self-sealing blood and body fluid collection tube for capillary collection of blood and other body fluids comprising a unitary tubular body having an elongated bore and a fluid entry end, and a super-absorbent containing composite material comprising a super-absorbent polymer and an organic support matrix provided within said tube opposite said fluid entry end, said super-absorbent material adapted to expand when contacted by one of blood and a body fluid and seal said tube to prevent passage of air and liquid through the plug during centrifugation and expulsion.

9. A self-sealing movable plug for use in a fluid collection tube, said plug provided with a vent channel extending therethrough, said plug being comprised of a super-absorbent containing composite material that will swell to seal said tube and be impermeable during centrifugation and expulsion to air and to liquids after said fluid contacts said vent channel of said plug.

10. The self-sealing plug of claim 9 wherein said plug comprises a super-absorbent material adapted to expand when contacted by said fluid.

11. The self-sealing plug of claim 10 wherein said super-absorbent material comprises a super-absorbent polymer and an organic support matrix.

12. The self-sealing plug of claim 11 wherein said super-absorbent polymer is an acrylic acid containing polymer.

13. The self-sealing plug of claim 11 wherein said organic support matrix is a member of the class consisting of organic polymers, fats, waxes, and thixotropic oils blended into a composite material.

14. The self-sealing plug of claim 9 wherein said plug comprises an acrylic acid polymer dispersed within a support polymeric organic support matrix.

15. The self-sealing plug of claim 9 wherein said fluid is a fluid containing at least two components having a different specific gravity and said plug has a specific gravity greater than the heaviest component of the fluid.

16. The self-sealing plug of claim 9 wherein said fluid is blood.

17. A system for the collection, separation and dispensation of an aqueous fluid containing at least two components having a different specific gravity comprising:
 (a) a unitary tubular body having an elongated bore and a fluid entry end, a plug of super-absorbent material provided within said tube opposite said fluid entry end, said plug having a specific gravity greater than the component of the fluid having the highest specific gravity, and at least one sealant material provided within said tube, said sealant material having a specific gravity intermediate that of at least two of the components of the fluid; and
 (b) dispensing means adapted to receive said fluid collection tube after the components of said fluid and sealant material within said tube have been separated, said dispensing means comprising:
  (i) a housing adapted to receive said tube;
  (ii) a rod member extending axially through said housing, said rod member sized to fit into said fluid collection tube;

(iii) an adjustment means connected to said rod member and said housing to permit movement of the rod member relative to the housing;

(iv) a plunger member connected to an end of said rod member, said plunger member extending outward from said housing; and (v) adjustable stop means provided on said plunger member, said stop means capable of being positioned at any desired one position of several positions on said plunger and adapted to permit said plunger to travel a calibrated distance into said housing, said calibrated distance being directly related to said desired one position of the stop means on said plunger.

18. The system in claim 17 wherein the fluid collection tube has a fluid collection chamber of a known volume and the dispensing means is adapted to expel a pre-determined volume of separated fluid.

19. The system of claim 18 also comprising a hydrophobic coating applied to the inner diameter of one end of said collection tube.

20. The system of claim 18, wherein said collection tube is a capillary tube having one end thereof flared outward.

21. The system of claim 18 wherein said dispensing means further comprises:
(a) a housing;
(b) a rod member extending axially through said housing, said rod member sized to fit into said fluid collection tube; and
(c) an adjustment means connected to said rod member and said housing to permit movement of the rod member relative to the housing.

22. The system of claim 21 wherein said adjustment means comprises:
(a) a plunger member connected to an end of said rod member opposite said plug means, said plunger member extending outward from said housing;
(b) stop means provided on said plunger member, said stop means adapted to permit said plunger member to travel a calibrated distance into said housing; and
(c) return means engaged on said plunger member, said return means adapted to fully extend plunger a calibrated distance out of said housing.

23. The system in claim 22 wherein said return means is a spring.

24. The system of claim 21 also comprising a plug attached to said rod member, said plug sized to fit into the fluid collection tube.

25. The system in claim 21 wherein said dispensing means further comprises a locking means which secures said collection tube within said housing.

26. The system in claim 17 further comprising identification means provided on said collection tube.

27. The system in claim 26 in which said identification means is at least one of a label applied on said collection tube and a label applied on a cap adapted to cover said collection tube.

* * * * *